(12) United States Patent
Huang et al.

(10) Patent No.: US 7,186,705 B2
(45) Date of Patent: Mar. 6, 2007

(54) PROCESS FOR THE PREPARATION OF 3-AMINO-2-HYDROXYPROPYLPHOSPHINIC ACID DERIVATIVES

(75) Inventors: Bao-Guo Huang, Bridgewater, NJ (US); Witold Subotkowski, Whitehouse Station, NJ (US); Duane Rudisill, Milford, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 295 days.

(21) Appl. No.: 10/946,869

(22) Filed: Sep. 22, 2004

(65) Prior Publication Data

US 2005/0070507 A1    Mar. 31, 2005

Related U.S. Application Data

(60) Provisional application No. 60/505,220, filed on Sep. 23, 2003.

(51) Int. Cl.
*A61K 31/66*    (2006.01)
*C07F 9/28*    (2006.01)

(52) U.S. Cl. ......................................... 514/114; 562/11
(58) Field of Classification Search ................ 514/114; 562/11
See application file for complete search history.

(56) References Cited

U.S. PATENT DOCUMENTS

| | | | |
|---|---|---|---|
| 5,229,379 A * | 7/1993 | Marescaux et al. | 514/114 |
| 5,300,679 A | 4/1994 | Baylis et al. | |
| 5,376,684 A * | 12/1994 | Mickel | 514/553 |
| 5,407,922 A * | 4/1995 | Marescaux et al. | 514/89 |
| 5,424,441 A | 6/1995 | Mickel et al. | |
| 5,500,418 A * | 3/1996 | Mickel | 514/100 |
| 5,545,631 A * | 8/1996 | Marescaux et al. | 514/89 |
| 5,567,840 A | 10/1996 | Hall et al. | |

OTHER PUBLICATIONS

Froestl et al., Phosphinic Acid Analogs of GABA. 2. Selective, Orally Active GABAB Antagonists, J. Med. Chem.; 1995; 38(17); 3313-3331.*

J. G. Dingwall et al., Diethoxymethylphosphonites And Phosphinates. Intermediates For The Synthesis Of alpha, beta- And omega-aminoalkylphosphonous Acids , Tetrahedron (1989, pp. 3787-3808, vol. 45, No. 12).

J. G. Dingwall et al., Synthesis Of gamma-aminoprophylphosphonous Acids Using Hypophosphorous Acid Synthons, Phosphorus And Sulfur (1987, pp. 571-574, vol. 30).

J. G. Dingwall, New Carboxyphosphonic And Phosphinic Acid Structures Of Technical And Biological Interest, Phosphorus And Sulfur (1983, pp. 353-356, vol. 18).

Michel Belley et al., Synthesis Of The Nanomolar Photoaffinity GABA (B) Receptor Ligand CGP 71872 Reveals Diversity In The Tissue Distribution of GABA (B) Receptor Forms, Bioorganic And Medicinal Chemistry (1999, pp. 2697-2704, vol. 7).

Petr Alexander et al., Synthesis Of 9-(2-Phosphinomethoxyethyl) Adenine And Related Compounds), Collection Of Czechoslovak Chemical Communications (1994, pp. 1870-1878, vol. 59).

Wolfgang Froestl et al., Ligands For Expression Cloning And Isolation Of GABA (B) Receptors, IL Farmaco (2003, pp. 173-183, vol. 58).

Wolfgang Froestl et al., Phosphinic Acid Analogues Of GABA. 2. Selective, Orally Active GABA beta Antagonists, J. Med. Chem. (1995, pp. 3313-3331, vol. 38).

Wolfgang Froestl et al., Phosphinic Acid Analogues of GABA. 1. New Potent And Selective GABA beta Agonists, J. Med. Chem. (1995, pp. 3297-3312, vol. 38).

* cited by examiner

*Primary Examiner*—Thurman K. Page
*Assistant Examiner*—Chukwuma Nwaonicha
(74) *Attorney, Agent, or Firm*—Balaram Gupta

(57) ABSTRACT

The present invention relates to a process for the preparation of 3-amino-2-hydroxypropylphosphinic acid derivatives of the formula I,

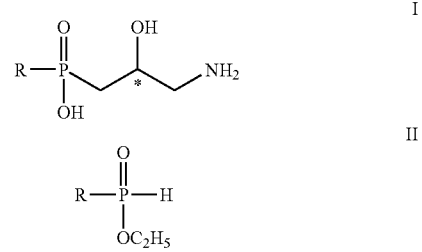

which are valuable pharmaceutical active ingredients and can be used, for example, as antidepressants. The process starts from O-ethyl phosphinates of the formula II into which, after silylation with hexamethyldisilazane, the 3-amino-2-hydroxypropyl moiety is introduced by reactions with epichlorohydrin and ammonia.

20 Claims, No Drawings

PROCESS FOR THE PREPARATION OF 3-AMINO-2-HYDROXYPROPYLPHOSPHINIC ACID DERIVATIVES

This application claims the benefit of U.S. Provisional Application No. 60/505,220, filed Sep. 23, 2003.

BACKGROUND OF THE INVENTION

1. Field of the Invention

The present invention relates to a process for the preparation of 3-amino-2-hydroxypropylphosphinic acid derivatives which are valuable pharmaceutically active ingredients and can be used, for example, as antidepressants.

2. Description of the Art

U.S. Pat. No. 5,300,679, and the articles of Froestl et al., J. Med. Chem. 38, 3297–3312 (1995) and Froestl et al., J. Med. Chem. 38, 3313–3331 (1995), all of which are incorporated herein by reference, disclose that 3-amino-2-hydroxypropylphosphinic acid derivatives possess valuable pharmacological properties such as a binding affinity to GABA (γ-aminobutyric acid) receptors, specifically to the GABA$_B$ receptor subtype, and can influence the release of excitatory amino acids and neurotransmission processes in the brain. Accordingly, a few of these compounds, which are antagonists of the GABA$_B$ receptor, are useful as pharmaceutically active ingredients for the treatment of disease states of the central nervous system like anxieties, depressions or impaired cognitive functions, i.e., they are useful as nootropic, antidepressive or anxiolytic agents. Of particular interest because of their property profiles are the GABA$_B$ receptor antagonists of the formula I in which R is a benzyl group or a cyclohexylmethyl group.

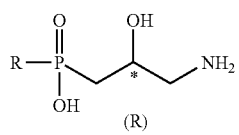

The process for the preparation of a compound which is used as a pharmaceutically active ingredient in a medicament and needed on an industrial scale has to fulfill various requirements. The process and the obtained product have to be in line with the regulatory requirements and have to be reproducible and validated. In particular, regulatory authorities stipulate a precise degree of purity of the obtained drug substance. On the other hand, a process performed on an industrial scale for the preparation of a marketed product should of course be as simple, cost and labor effective as possible. If possible, it should thus avoid the use of expensive starting materials, physiologically unacceptable toxic materials, difficult technical operations, long reaction times, or a large number of procedural steps, for example. In this respect, the known processes for the preparation of compounds of the formula I have considerable drawbacks which render them hardly suitable for a production on a large scale.

In the article of Froestl et al., J. Med. Chem. 38, 3313–3331 (1995) a process for the preparation of hydrochlorides of the racemic compounds of formula I in which R is benzyl or cyclohexylmethyl is disclosed. The method disclosed therein utilizes corrosive starting materials such as chlorotrimethylsilane, which is especially not suitable for a commercial operation. Furthermore, this method involves a number of steps thus rendering it unsuitable for a commercial operation. More importantly, a several of the intermediates formed therein need to be purified by column chromatography before they can be used in the subsequent steps.

Froestl et al., J. Med. Chem. 38, 3313–3331 (1995) also discloses a process for the preparation of enantiomerically pure 3-amino-2-hydroxypropylphosphinic acid derivatives utilizing the appropriate chiral epichlorohydrin. This method also suffers from all of the same problems discussed above. That is, undesirable starting materials such as chlorotrimethylsilane and a need for purifying the intermediates by column chromatography.

Most importantly, several of these processes utilize various other substances which are unsuitable for preparing pharmaceutical grade end-products. For instance, Froestl et al., employ propylene oxide to convert the hydrochloride of the final product to free amine. It is well known that propylene oxide is a known carcinogen and therefore it is beneficial to avoid such materials in the preparation of a pharmaceutically active ingredient. Similarly, a few of these processes utilize solvents which are not advantageous in the preparation of pharmaceutically active compounds, for example, use of solvents such as tetrahydrofuran is undesirable.

Various other drawbacks of these known processes are also evident. For example, several steps in these processes require long reaction times, which lead to a very low time-space yield. The necessity to filter the suspension containing the moisture-sensitive silyl intermediate requires special technical devices and thus increased cost of operation. Thus, there is a need for a simpler and improved process for the production of the compounds of formula I. The present invention satisfies this need by providing such a process.

SUMMARY OF THE INVENTION

An object of the present invention is to provide an improved process for the preparation of a compound of the formula I in which R is benzyl or cyclohexylmethyl, or a salt thereof, from a compound of the formula II in which R is benzyl or cyclohexylmethyl.

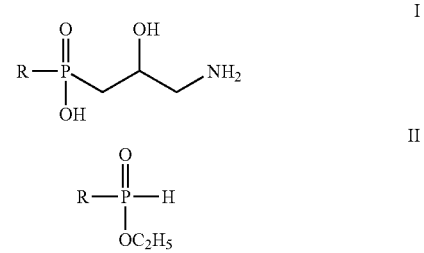

The process starts from O-ethyl phosphinates of the formula II which are first silylated with hexamethyldisilazane, the silylation products are then reacted with epichlorohydrin, with ammonia, hydrolysis of the ethyl phosphinate moiety and optional conversion of a salt of the compound of formula I obtained into the compound of formula I. Advantageously, all of these operations can be performed in a single batch operation.

DETAILED DESCRIPTION OF THE INVENTION

The terms as used herein have the following meanings:

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds, according to the invention, possess two or more asymmetric centers, they may additionally exist as diastereoisomers; also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

In more detail, the process of the invention can be practiced, for example, following the sequences as depicted in Scheme 1. First, a compound of the formula II is reacted with hexamethyldisilazane, optionally in the presence of a catalyst, to give the silylation product of formula III which is then reacted either with (S)-epihalohydrin or (R)-epihalohydrin in the same pot, optionally in the presence of a catalyst. As an intermediate the compound of formula IV may be obtained which is desilylated to give the intermediate of formula V. The latter is then reacted with ammonia to give the intermediate of formula VI. The ethyl phosphinate moiety in compound of formula VI is hydrolyzed to give the phosphinic acid of formula I or, for example, a salt thereof such as an acid addition salt of formula VII in which HX denotes a hydrohalic acid and which can optionally be converted into the compound of formula I. Examples of hydrohalic acids include hydrofluoric acid, hydrochloric acid, hydrobromic acid, and hydroiodic acid. Generally, hydrochloric acid is preferred. However, various other organic and/or inorganic acids can also be used in place of an hydrohalic acids. Examples of such organic acids include, without any limitation, acetic acid, maleic acid, oxalic acid, methanesulfonic acid, p-toluenesulfonic acid, and the like. Suitable inorganic acids include, without any limitation, sulfuric acid, nitric acid, phosphoric acid, and the like.

Advantageously, it has now been found that all of the intermediates, i.e., compounds of formulae III to VI can be used as such in the subsequent steps without any further purification. Thus the present method offers an improved efficiency in the preparation of compounds of formula I in high yields and in high purities yet requiring no expensive column chromatographic purification as used in the prior art references cited herein. The purification may be carried out at the final step in order to obtain high purity crystalline product. Therefore, this method of the invention is best suited for a commercial scale-up operation.

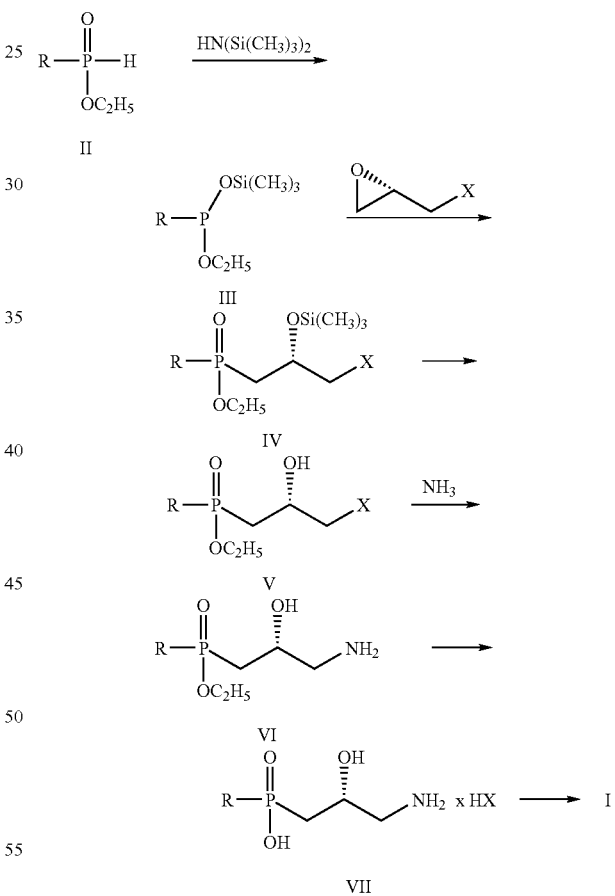

Scheme 1

The starting compounds of the formula II are commercially available or can be prepared according to known procedures, for example, according to the procedures described or referred to in U.S. Pat. No. 5,300,679 and the articles of Froestl et al., J. Med. Chem. 38, 3297–3312 (1995) and Froestl et al., J. Med. Chem. 38, 3313–3331 (1995). Thus, the compounds of the formula II may be obtained by alkylation of ethyl (diethoxymethyl)-phosphinate or ethyl (1,1-diethoxyethyl)phosphinate, which are available from triethyl orthoformate or triethyl orthoacetate and phosphinic acid, with a benzyl halide such as benzyl bromide or a cyclohexylmethyl halide in the presence of a base, for example sodium hydride, optional conversion of the benzylphosphinic derivative into the (cyclohexylmethyl)-phosphinic derivative by catalytic hydrogenation, cleavage of the diethoxymethyl group or 1,1-diethoxyethyl group, for example, by refluxing with hydrochloric acid, and, if necessary, re-esterification of the phosphinic acid, for example, with ethyl chloroformate.

The silylation of the compound of formula II with hexamethyldisilazane to give the intermediate of formula III can be performed by mixing the compound of formula II with the desired amount of hexamethyldisilazane in a dry reactor under an inert atmosphere and reacting the mixture until the desired conversion rate has been achieved., In general, the hexamethyldisilazane is employed from about an equimolar amount to about 10 fold molar excess amount with respect to molar amount of the compound of formula II. Preferably the hexamethyldisilazane is employed in excess, for example, from about 2 fold excess to about 12 fold molar excess amount or from about 3 fold excess to about 10 fold molar excess amount. More preferably, hexamethyldisilazane is employed in about 5 fold molar excess amount with respect to the molar amount of the compound of formula I.

Any of the reaction temperatures that may bring about the intended result can be employed in this step of the invention. Preferably the reaction with hexamethyldisilazane is carried out above room temperature and with heating. More preferably it is carried out at temperatures from about 80° C. to about 160° C. or from about 100° C. to about 140° C. or from about 120° C. to about 140° C. The reaction can be carried out under atmospheric pressure or at lower or higher pressure. Favorably the reaction is carried out by heating the reaction mixture under reflux at a temperature of about 125° C. at about atmospheric pressure. The reaction can be carried in the absence or in the presence of an additional inert solvent or diluent. Preferably it is carried out without an additional solvent or diluent. The reaction time depends on the employed reaction conditions, the scale of the reaction and the desired degree of conversion. An appropriate time may be, for example, from about 2 hours to about 30 hours, for example from about 16 hours to about 30 hours. The progress of the reaction can be monitored, for example, spectroscopically or chromatographically or by observing the evolution of the by-product ammonia.

The reaction of the compound of the formula II with hexamethyldisilazane can be carried out in the absence or in the presence of a catalyst. Preferably the reaction is carried out in the presence of a catalyst. Suitable catalysts include ammonium salts, in particular ammonium salts of strong acid such as mineral acids, for example ammonium sulfate, ammonium chloride or ammonium salts of sulfonic acids such as toluenesulfonic acid or methanesulfonic acid, and compounds whose addition to the reaction mixture leads to the formation of ammonium salts, for example acids including sulfuric acid and sulfonic acids such as toluenesulfonic acid or methanesulfonic acid, or silyl halides such as chlorotrimethylsilane. A preferred catalyst for the reaction of the compounds of formula II with hexamethyldisilazane is ammonium sulfate $((NH_4)_2SO_4)$.

The appropriate amount of the catalyst depends on the circumstances of the individual preparation. In general, from about 0.01 fold to about 0.3 fold molar amount or from about 0.02 fold to about 0.25 fold molar amount or from about 0.02 fold to about 0.15 fold molar amount or from about 0.03 fold to about 0.10 fold molar amount of catalyst, with respect to the employed molar amount of compound of the formula II, may be appropriate. The catalyst may be added in one portion or in two or more portions at the beginning of the reaction and/or during the course of the reaction.

When the desired degree of conversion of the compound of the formula II into the silylated intermediate of the formula III has been achieved, any work-up procedures or purification steps may follow, if desired. For example, any volatiles may be removed by heating and/or applying reduced pressure, or any solids may be removed by filtration. Specifically, unreacted hexamethyldisilazane may be distilled off, for example in vacuo, if desired. However, surprisingly, as noted above, it was found that for carrying out the subsequent reaction with epihalohydrin it is not necessary to remove excess hexamethyldisilazane or the catalyst from the silylated intermediate of formula III or perform any other work-up procedures at this stage of the preparation of the compound of formula I. Accordingly, after cooling to about room temperature, the reaction mixture as is can directly be employed into the subsequent reaction without giving rise to unacceptable side reactions or loss of yield of the desired product. Any additional handling of the moisture-sensitive intermediate of formula III, such as the removal of triethylammonium chloride by filtration in the prior art process for the production of the compound of formula I, which would require special devices and may lead to partial decomposition of the compound of formula III, can thus be avoided. Accordingly, in a preferred embodiment of the present invention the silylated intermediate of formula III is not isolated and the reaction mixture of the silylation of the compound of formula II with hexamethyldisilazane is not subjected to additional work-up procedures or purification procedures, but the reaction mixture is directly employed into the subsequent reaction with epihalohydrin as is.

The reaction of the compound of formula III with epihalohydrin can be performed by initially admixing the compound of formula III, preferably the reaction mixture obtained in the previous silylation step, with the desired amount of the epihalohydrin. Various known epihalohydrins can be employed in this process of the invention. Examples of suitable epihalohydrins include, without any limitation, (S)- or (R)-epifluorohydrin, (S)- or (R)-epichlorohydrin, (S)- or (R)-epibromohydrin or (S)- or (R)-epiiodohydrin.

Preferably, the compound of formula (III) is reacted with either (S)-epichlorohydrin or (R)-epichlorohydrin of the desired optical purity under an inert atmosphere and with the exclusion of moisture, and under the desired reaction conditions. If desired, part or all of the epichlorohydrin can be added in one or more portions or continuously over a certain period of time during the course of the reaction. In general, the epichlorohydrin is employed in an equimolar amount to about 1.5 fold molar excess amount, with respect to molar amount of the compound of formula III or the similar molar amount of compound of the formula II which had been employed into the preparation of the compound of formula III. Preferably the epichlorohydrin is employed in excess, for example, from about 1.05 fold to about 1.5 fold molar amount.

Preferably the reaction of the compound of the formula III with epichlorohydrin is carried out in the presence of a catalyst. Suitable catalysts include Lewis acids, for example metal halides such as zinc chloride $ZnCl_2$. As usual, the appropriate amount of the catalyst depends on the circumstances of the individual preparation. In general, from about 0.02 fold to about 0.2 fold molar amount or from about 0.05 fold to about 0.2 fold molar amount or from about 0.05 fold to about 0.15 fold molar amount of catalyst, with respect to the employed molar amount of epichlorohydrin, may be appropriate. The catalyst may be added in one portion to the compound of formula III or the reaction mixture obtained in the previous step or to the reaction mixture already containing the epichlorohydrin, or it may be added in two or more portions at the beginning of the reaction and/or during the course of the reaction of the compound of formula III with epichlorohydrin. It may also be added continuously over a certain period of time.

The reaction of the compound of formula III with epichlorohydrin can be carried out in the absence or in the presence of an additional inert solvent or a diluent. Preferably it is carried out without an additional solvent or diluent. Examples of solvents or diluents which may be employed, if desired, include aliphatic and aromatic hydrocarbons and chlorinated hydrocarbons and acyclic and cyclic ethers such as tetrahydrofuran. The reaction may be performed in such a manner that initially a solvent or diluent is present in the reaction mixture, for example, for allowing an easier addition of the epichlorohydrin and/or of the catalyst which may be introduced into the reaction vessel in the form of a solution or suspension, or for allowing an easier control of the reaction, and that during the course of the reaction the solvent or diluent is removed by heating and/or applying reduced pressure.

Depending on the circumstances and the scale of the individual preparation, the reaction of the compound of formula III with epichlorohydrin may proceed exothermically, and care has to be taken to control the course of the reaction and to avoid a too violent course by carefully monitoring the temperature of the reaction mixture and adjusting the heating or cooling and the addition of the reactants and/or of the catalyst appropriately. Preferably the reaction of the compound of formula III with epichlorohydrin is carried out at temperatures from about 0° C. to about 100° C., more preferably from about room temperature to about 80° C.

In a preferred embodiment of the invention, a catalyst or part of the catalyst and the epichlorohydrin or part of the epichlorohydrin are added at about room temperature to the compound of formula III or the reaction mixture obtained in the previous step. The resulting mixture is slowly heated to about 50° C. and, if a violent reaction does not occur, it is then further heated to about 80° C. and held at about 80° C. until the desired degree of conversion. Optionally during the heating or at any temperature range maintained for a certain time during the heating remaining parts of the catalyst and/or of the epichlorohydrin may be added. In general, after heating of the reaction mixture to about 80° C. for about 1 to 4 hours, for example, 2 hours, the reaction is complete. The progress of the reaction can be monitored, for example, spectroscopically or chromatographically.

When the desired degree of conversion of the compound of the formula III has been achieved, the reaction mixture may be worked up. Alternatively, the resulting silyl intermediate of formula IV may be desilylated directly to the intermediate of formula V. For example, at this stage unreacted hexamethyldisilazane can be removed by distillation in vacuo, for example, at about 40° C. to about 50° C., and the concentrated reaction mixture then subjected to aqueous work-up by partitioning between an aqueous phase and a suitable organic solvent, for example, a hydrocarbon or chlorinated hydrocarbon or ester or ether, in order to remove by-products, unreacted starting material and/or catalyst. Conveniently the concentrated reaction mixture is partitioned between aqueous ammonia solution, for example about 15% ammonia solution, and dichloromethane, and the obtained solution of the product in dichloromethane is concentrated in vacuo. For conversion of silylated intermediate of formula IV into the compound of formula V the residue can then be treated with a dilute acid. Favorably, a dilute solution of a strong acid, for example, a mineral acid such as hydrochloric acid, in an organic solvent, for example a lower alkanol such as methanol or ethanol, is employed, for example a 1% (volume by volume) solution of concentrated aqueous hydrochloric acid in methanol. Under such conditions the desilylation of the compound of formula IV to the compound of formula V can be achieved smoothly by stirring the mixture at room temperature for about 30 minutes to about 1 hour and thus considerably faster than by means of acetic acid. After concentration of the mixture, for example, at about 40° C. to about 50° C. in vacuo, crude ethyl 3-chloro-2-hydroxypropylphosphinate of formula V is obtained which can advantageously be used in the subsequent reaction without further purification.

For the amination to give the compound of formula VI, the product obtained in the previous step is combined with ammonia. Usually an excess of ammonia, for example, from about 10 fold to about 30 fold molar excess amount or from about 15 fold to about 25 fold molar excess amount of ammonia, with respect to amount of the compound of formula V or with respect to the initial starting compound of formula II, is employed. The reaction can be carried out in the absence or in the presence of an additional inert solvent or diluent. Preferably it is carried out in the presence of one or more additional solvents or diluents, for example in the presence of one or more inert organic solvent such as lower alkanols, for example, methanol or ethanol or isopropanol, or cyclic or acyclic ethers.

Preferably the amination is carried out at about room temperature or at a temperature from about 10° C. to about 30° C. In a convenient manner of performing the amination, a solution of the compound of formula V in a solvent such as ethanol is placed in a pressure reactor and the desired amount of ammonia is introduced. Preferably the solution of the compound of formula V is initially cooled to a temperature below the boiling point of ammonia, for example, to a temperature from about −50° C. to about −35° C., and liquid ammonia is introduced. The closed reactor is then allowed to warm-up with the autogenous pressure building up which depends on the circumstances of the individual preparation and may be in the range of from about 30 psi to about 60 psi or from about 35 psi to about 50 psi. An appropriate reaction time may be, for example, from about 3 days to about 5 days, for example about 4 days. When the desired degree of conversion of the compound of formula V into compound of formula VI has been achieved, the reaction mixture may be worked up, after cooling and/or releasing the pressure, by filtering off any solids such as the formed ammonium chloride, and distilling off any volatiles, for example, at about 40° C. to about 60° C. in vacuo. The residual crude amination product can advantageously be employed into the hydrolysis of the ethyl phosphinate moiety without further purification.

After the amination step, the hydrolysis of the ethyl phosphinate moiety to the phosphinic acid derivative of formula I or a salt thereof may be performed under basic or acidic conditions. Preferably the hydrolysis is performed under acidic conditions in the presence of a strong acid such as a mineral acid, for example hydrochloric acid, at elevated temperature. Preferably the anion of the employed acid is a physiologically acceptable, non-toxic anion. Besides water, one or more additional inert organic solvents or diluents, for example lower alkanols such as methanol or ethanol, may be present during the hydrolysis of the ethyl phosphinate. Preferably the hydrolysis is performed by heating the ethyl phosphinate in the absence of an additional solvent or diluent with a concentrated aqueous solution of a strong acid, for example, by heating it with concentrated aqueous hydrochloric acid containing about 30 to about 40% (weight by weight) of hydrogen chloride. Generally the acid employed is in excess when compared with amount of compound of formula VI. The appropriate amount depends on the circumstances of the individual preparation. For example, if the ethyl phosphinate is hydrolyzed with concentrated hydrochloric acid (37%) without an additional solvent or diluent, about 3 fold excess amount by weight of the acid, with respect to the amount by weight of the employed ethyl phosphinate, may be appropriate. The acidic hydrolysis is usually carried out at temperatures from about 80° C. to about 120° C. or from about 80° C. to about 100° C. or from about 90° C. to about 100° C. at about atmospheric pressure or higher pressure. Favorably, the hydrolysis is carried out in an aqueous system by heating the reaction mixture under reflux at a temperature of about 100° C. at about atmospheric pressure. The appropriate reaction time depends on the circumstances of the individual preparation and may be from about 2 to about 6 hours, for example about 4 hours.

The product initially isolated after acidic hydrolysis of the ethyl phosphinate moiety may be an addition salt of the compound of formula I, i.e. a compound of formula VII in which the acid HX usually is the acid used in the hydrolysis step. As indicated, the anion X of the acid HX in the salt of formula VII preferably is a physiologically acceptable, non-toxic anion which may be present in a medicament if desired. When performing the hydrolysis by means of hydrochloric acid, initially the hydrochloride of the compound of formula I, i.e. is the compound of formula VII in which HX is HCl, may be isolated. Depending on whether it is intended to produce the free compound of formula I or a salt thereof and whether it is intended to perform subsequently any specific steps such as a purification with the compound of formula I or with a salt thereof, it may be more convenient to isolate a salt of the formula VII after acidic hydrolysis of the ethyl phosphinate or to convert the salt directly into the compound of formula I and isolate the latter.

In a preferred embodiment of the present invention, after completion of the acidic hydrolysis of the ethyl phosphinate, a salt of the formula VII is isolated, preferably the hydrochloride of formula VII in which X is Cl after hydrolysis with hydrochloric acid. For isolation of the salt, standard work-up procedure may be applied. For example, the reaction mixture may be concentrated, for example, by evaporation at about 40° C. to about 80° C. in vacuo, and/or cooled and/or admixed with one or more solvents or diluents, and the obtained product isolated by filtration or centrifugation. The isolated salt may then be subjected to any purification steps, for example, recrystallization, and/or converted into the free compound of formula I.

If desired, a salt of the compound of formula I such as an acid addition salt of formula VII obtained after hydrolysis of the ethyl phosphinate moiety may be converted into the free compound of formula I. To this end, an acid addition salt of formula VII can be treated in a solvent or a diluent with an agent which binds or scavenges the acid HX. In choosing such an agent for a large-scale conversion into the free compound of formula I with the required purity for use of the product as a drug substance, various aspects have to be taken into account including the sensitivity of the compounds to certain reaction conditions, the solubilities of the salt of formula VII, the compound of formula I, the agent, the by-product formed from the agent and the acid HX, and of impurities, and further aspects such as the toxicological acceptability of the agent and the by-product formed from the agent and the acid HX for use in the final step of the production of a clinically used drug substance. For instance, traditionally, the salt of formula VII, particularly hydrochloride, is treated with an acid scavenger such as propylene oxide to form the free amine of formula I. As noted earlier, this approach is especially unsuitable in the preparation of a drug substance since any contamination of propylene oxide is undesirable in such uses as it is a known carcinogen.

It has now been found that the conversion of an acid addition salt of the formula VII, in particular of the hydrochloride of the formula VII in which X is Cl, into the compound of formula I can conveniently be accomplished by treatment with a suitable amine such as a di(lower alkyl)amine or tri(lower alkyl)amine, in particular a tri (lower alkyl)amine such as, for example, triethylamine, in a solvent or diluent such as a lower alkanol, for example, methanol or ethanol, or water or a mixture of two or more solvents or diluents, in particular in methanol.

In a preferred embodiment of the present invention the compound of formula VII, for example, the compound of formula VII in which X is Cl, is dissolved or suspended in an appropriate amount of a solvent, for example methanol, an appropriate amount of an amine, for example, triethylamine is added and the formed free compound of formula I is isolated by standard work-up procedures, for example, filtration or centrifugation of precipitated compound of the formula I, optionally after concentration and/or cooling and/or admixing with another solvent or diluent. The compound of formula I obtained in such a way is highly pure and does not require unacceptable purification steps such as chromatography. The fact that by the process of the present invention the compound of formula I can be prepared in high quality without extensive purification of any of the intermediates, in particular without a chromatography, is surprising and constitutes a substantial advantage over the prior art processes for its preparation. If desired, the obtained compound of formula I can be purified further by easily performed procedures such as washing or dissolution/precipitation with a solvent, for example, water or acetone or a lower alkanol such as methanol or ethanol or a mixture of solvents, at room temperature or elevated temperature, for example, at the boiling point of the solvent, and/or recrystallization, for example, from the above mentioned solvents such as from a mixture of water and acetone, and drying.

More specifically, the compound of formula I in which R is cyclohexylmethyl can be purified by dissolving it in water and then precipitating it from acetone. Typically, the dissolution of the compound of formula I can be done at ambient or superambient temperatures. Preferably such dissolution can be carried out at a temperature range of from about 70° C. to about 85° C. The clear solution is then allowed to cool to a temperature from about 40° C. to about 60° C. The solution may be filtered to remove any insoluble impurities. Then the compound of formula I is precipitated in high purity by the addition of acetone. Finally, if desired, for use in the production of pharmaceutical compositions, the obtained compound of formula I may be milled.

The amine used for liberating the free compound of formula I can be combined with the salt of formula VII at about room temperature or at a lower temperature or a higher temperature, for example, at a temperature from about room temperature to about 60° C. or from about room temperature to about the boiling point of the solvent. Preferably the amount of solvent and the temperature are chosen such that the compound of formula VII is completely dissolved to provide a clear solution before the amine is added. Favorably, the amine is added at room temperature or at about 10° C. to about 30° C. In general, the amine is employed in about equimolar amount to about 2 fold molar excess amount, with respect to molar amount of the salt of formula VII. Preferably the amine is employed in slight excess, for example, from about 1.05 fold to about 1.5 fold molar excess amount or from about 1.1 fold to about 1.4 fold molar excess amount.

Thus in accordance with the practice of this invention the compound of formula I can be prepared especially in an industrial scale essentially in the absence of any toxic materials. Additionally, the by-products formed such as triethylammonium chloride can be readily separated as it is soluble in methanol, the solvent employed herein. Altogether, the process of the present invention which is based on surprising findings with respect to reactivities and properties of involved compounds, allows the preparation of the compounds of formula I or salts thereof in high quality, for example, with a chemical purity of 99% or more and an optical purity of 99.5% or 99.8% enantiomeric excess or more, in a simpler manner than the known processes and is considerably better applicable on an industrial scale.

A subject of the present invention also is a compound of the formula I in which R is benzyl or cyclohexylmethyl, or a salt thereof, in particular the compound of formula I which is (3-amino-(2R)-hydroxypropyl)(cyclohexylmethyl)phosphinic acid, which has been obtained by the process of the present invention.

In one embodiment of the present invention R is cyclohexylmethyl. In another embodiment of the present invention R is benzyl. Besides as active pharmaceutical ingredient, a compound of the formula I in which R is benzyl, or a salt thereof, can also be used as an intermediate in the preparation of a compound of the formula I in which R is cyclohexylmethyl, or a salt thereof, by catalytic hydrogenation of the phenyl moiety to give the cyclohexyl moiety, for example by hydrogenation in the presence of a noble metal catalyst such a platinum dioxide. The hydrogenation of the phenyl moiety to give the cyclohexyl moiety may also be performed on the stage of an intermediate in the process of the present invention.

In one embodiment of the present invention the chiral carbon atom in the 3-amino-2-hydroxypropyl moiety in the compounds of formula I is present with uniform R configuration or substantially uniform R configuration and the respective compound of the formula I is a compound of the formula Ia in which R is benzyl or cyclohexylmethyl.

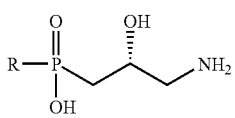

Ia

In another embodiment of the present invention the chiral carbon atom in the 3-amino-2-hydroxypropyl moiety in the compounds of formula I is present with uniform S configuration or substantially uniform S configuration and the respective compound of the formula I is a compound of the formula Ib in which R is benzyl or cyclohexylmethyl.

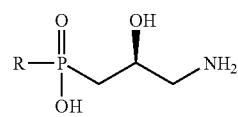

Ib

For the preparation of a compound of formula I in which the chiral carbon atom is present with R configuration, (S)-epichlorohydrin is employed as the starting material. For the preparation of a compound of formula I in which the chiral carbon atom is present with S configuration, (R)-epichlorohydrin is employed as the starting material. In a preferred embodiment, the present invention relates to the preparation of the compound of formula I in which R is cyclohexylmethyl and the chiral carbon atom in the 3-amino-2-hydroxypropyl moiety is present with uniform R configuration or substantially uniform R configuration, i.e. (3-amino-(2R)-hydroxypropyl)(cyclohexylmethyl)phosphinic acid of formula Ic, or a salt thereof.

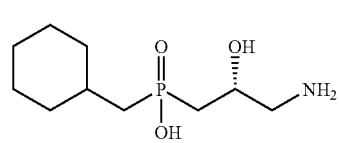

Ic

In another preferred embodiment, the present invention relates to the preparation of the compound of formula I in which R is benzyl and the chiral carbon atom in the 3-amino-2-hydroxypropyl moiety is present with uniform R configuration or substantially uniform R configuration, i.e. (3-amino-(2R)-hydroxypropyl)(benzyl)phosphinic acid of formula Id, or a salt thereof.

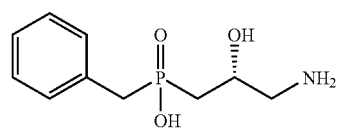

Id

In yet another preferred embodiment, the present invention relates to the preparation of the compound of formula I in which R is cyclohexylmethyl and the chiral carbon atom in the 3-amino-2-hydroxypropyl moiety is present with uniform S configuration or substantially uniform S configuration, i.e. (3-amino-(2S)-hydroxypropyl)(cyclohexylmethyl)phosphinic acid of formula Ie, or a salt thereof.

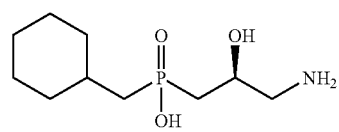

Ie

In yet another preferred embodiment, the present invention relates to the preparation of the compound of formula I in which R is benzyl and the chiral carbon atom in the 3-amino-2-hydroxypropyl moiety is present with uniform S configuration or substantially uniform S configuration, i.e. (3-amino-(2S)-hydroxypropyl)(benzyl)phosphinic acid of formula If, or a salt thereof.

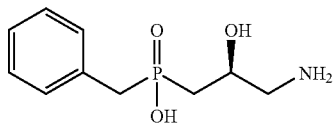

If

Finally, in yet another preferred embodiment, the present invention relates to the preparation of a compound of the formula Ic.

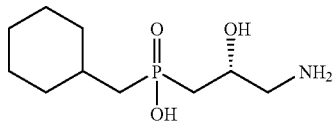

Ic

In this embodiment of the invention, the process first involves reacting a compound of the formula IIc with hexamethyldisilazane. This reaction can conveniently be carried out in the presence of a suitable catalyst and using any of the procedures described herein.

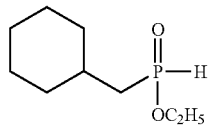

IIc

This reaction results in a compound of formula IIIc:

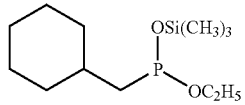

IIIc

The compound of formula IIIc is then reacted with (S)-(+)-epichlorohydrin. The resulting product is subsequently hydrolyzed to form a compound of formula Vc:

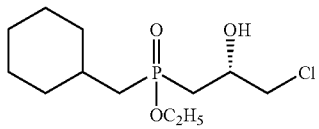

Vc

The compound of formula Vc is then reacted with ammonia and subsequently the ethyl phosphinate moiety is hydrolyzed to form the compound of formula Ic as its hydrochloride. In the final step, the hydrochloride of compound of formula Ic is treated with an amine such as triethylamine to form the compound of formula Ic.

With respect to tautomeric forms of the compounds involved in the present invention, including the compounds of formula I and starting materials and intermediates, it is understood that the present invention relates to all tautomers and mixtures of tautomers in any ratio. For example, the present invention relates to compounds of formula I when present in the form depicted in formula I or in the zwitterionic form or betain form depicted in formula Ig, in which R is benzyl or cyclohexylmethyl, or in the form of a mixture thereof in any ratio.

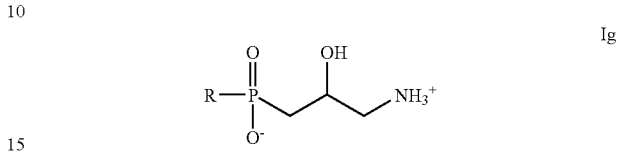

Ig

Just so, it is understood that with respect to all compounds involved in the present invention, including the compounds of formula I and starting materials and intermediates, the present invention relates to all stereoisomeric forms at the phosphorus atom. Thus, if a compound is involved in the invention which contains a chiral phosphorus atom, the present inventions relates to all possible stereoisomers of the compounds of the formula I and starting materials and intermediates including enantiomers and diastereomers and mixtures of two or more stereoisomers in any ratio.

This invention is further illustrated by the following examples which are provided for illustration purposes and in no way limit the scope of the present invention.

EXAMPLES

In the Examples that follow, the following abbreviations are used:
TLC Thin Layer Chromatography
HPLC High Performance Liquid Chromatography
GC/MS Gas Chromatography/Mass Spectroscopy
NMR Nuclear Magnetic Resonance Spectroscopy
MeCN Acetonitrile General Procedures Proton NMR ($^1$H NMR) spectra were recorded on a Varian Gemini instrument (300 MHz) with tetramethylsilane (0.00 ppm) or the solvent peak as a reference. Phosphorous NMR ($^{31}$P NMR) spectra were recorded on a Varian Gemini instrument (121 MHz) with $H_3PO_4$ as an external standard. Carbon NMR ($^{13}$C NMR) spectra were recorded on a Varian Gemini instrument (75 MHz). Chemical shifts are reported in parts per million (ppm). The following abbreviations are used in summarizing the NMR data: s=singlet, d=doublet; t=triplet; q=quartet; m=multiplet; dd=doublet of doublets; br=broad. Mass spectra were obtained on a Finnigan MAT TSQ 700 mass spectrometer using electron impact (EI) at 70 eV and chemical ionization (CI) with the relative peak height in percent and the molecular ion designated as M given in parentheses. Karl Fischer titration and elemental analyses were performed by Robertson Microlit, Inc. Madison, N.J.

Various other abbreviations used in the following Examples shall have the following meanings unless otherwise indicated: "$[\alpha]^{20}_D$" refers to specific rotation of the D line of sodium at 20° C. obtained in a 1 decimeter cell, "c" refers to concentration, "kg" refers to kilograms, "g" refers to grams, "mol" refers to moles, "mmol" refers to millimoles, "L" refers to liters, "mL" or "ml" refers to milliliters, "μL" refers to microliters, "° C." refers to degrees Celsius, "h" or "hr" refers to hours, "min" refers to minutes, "sec"

refers to seconds, "$t_R$" refers to retention time, "N" refers to normal, "psi" refers to pounds per square inch, "eq." refers to equivalent.

Analytical TLC was performed on glass-backed silica gel 60F-254 plates (EM) that were 0.25 mm thick, eluted with (v/v) solvent systems as described, and sprayed with a 5 wt % solution of phosphomolybdic acid in ethanol. TLC plates were then heated on a hot plate to show dark-blue spots.

GC/MS method: Hewlett Packard 5890 Series II gas chromatograph, Hewlett Packard 5972 Series mass selective detector, column: HP-5/MS, 30 m×0.32 mm×0.25 mm, non-polar, temperature range 0–300° C. GC program: initial temperature: 50° C., hold for 1 min: ramp: 20° C./min, final temperature: 300° C., hold for 5 min.

Analytical HPLC was carried out using one of the following methods:

Method A: Waters pump (600), Waters differential refractometer (410), RI detector settings: scale factor=20, sensitivity=2, oven temperature=35° C. Phenomenex Luna C18(2), 4.6×150 mm, 5 μm; Isocratic MeCN/$H_2O$ (30/70); 1 mL/min; injection volume: 20 μL.

Method B: Waters pump (600E), Waters 996 photodiode array detector monitored at 200 nm. Sample preparation: dissolve 4 mg of the sample (compound of formula I) in 1 mL of deionized $H_2O$. Column: Synergi-Polar RP 80A (Phenomenex, p/n: 00F-4336-E0) 4 μm, 4.6×150 mm. Mobile phase: 100% deionized $H_2O$, Flow Rate: 1 ml/min. Column Temp. 30° C., Injection volume: 20 μL, Run time: 25 min.

Method C: Column: Zorbax SB-C18 4.6×150 mm 3.5μ (P/N 830990-902 (Agilent)) Mobile phase: 55% $H_2O$, 45% MeOH, 2.5 mM Sodium dodecylsulfate, 10 mM $H_2SO_4$; Detector: UV 248 nm, Flow: 1.0 mL/min, Column temperature: 35° C. Preparation of solutions used for derivatization: GITC, 1 mg/ml: Dissolve 4 mg of 2,3,4,6-tetra-O-acetyl-β-D-glucopyranosyl isothiocyanate (TAGIT, Sigma T-5783) in 4 ml MeCN. Use within 2 days. pH 10 Buffer, 16 mM: Dissolve 134 mg $NaHCO_3$ in 100 mL $H_2O$. Adjust to pH 10 with NaOH. Drug substance solution, 4 mg/ml: Dissolve 4 mg of the compound of formula I in 1.0 mL of $H_2O$. Procedure for derivatization: Add 20 μL DS solution, 200 μL buffer, and 400 μL GITC to an HPLC vial. Cap, swirl, and wait 40 min. Reaction mixtures are stable for at least 6 h. Analysis: Injection Volume: 4 μL=2 μg sample, Run time: about 38 min., Retention time: (S)-enantiomer derivative, about 32 min; (R)-enantiomer derivative, about 35 min.

Concentration of the reaction solutions were performed using a Büchi Rotary Evaporator at 40° C. under reduced pressure from 50 to 30 torr unless otherwise indicated.

Example 1

O-Ethyl (3-chloro-(2S)-hydroxypropyl)(cyclohexylmethyl)phosphinate

O-ethyl (cyclohexylmethyl)phosphinate (12 kg, 63 mol; from Avecia), hexamethyldisilazane (50.55 kg, 313.2 mol), and ammonium sulfate (420 g, 3.18 mol) were charged to a 30 gallon glass lined reactor which had been dried and purged with nitrogen. The mixture was heated to and held at 128° C. for 20 h under a nitrogen flow. Additional ammonium sulfate (120 g, 0.91 mol) was added and the mixture heated at reflux for another 6 h to drive the reaction to completion (about 85% conversion by $^{31}P$ NMR). The reaction mixture was cooled to 25° C. and zinc chloride (900 g, 6.6 mol) and (S)-(+)-epichlorohydrin (6.3 kg, 68 mol; from Rhodia-Chirex, UK) were added in a single portion. The mixture was slowly warmed to 50° C. and monitored for any exothermic reaction. The mixture was then heated to and held at 80° C. for 2 h. After completion of the reaction (checked by GC) the mixture was concentrated at 45° C./50 torr to remove excess hexamethyldisilazane. The resulting residue was transferred to a 30 gallon hastalloy reactor and stirred with 60 L of 15% aqueous ammonia solution for 30 min to remove zinc chloride and small amounts of unreacted starting material. The mixture was then extracted with dichloromethane (two times, 35 L each). The combined extracts were washed with water (30 L) and the phases were separated. The aqueous phase was extracted with dichloromethane (20 L). The combined organic phases were concentrated at 45° C./100 torr to give O-ethyl (3-chloro-(2S)-trimethylsilyloxypropyl)(cyclohexylmethyl)phosphinate ($^{31}P$ NMR: δ 56.5 and 58.0; GC: $t_R$=10.29 and 10.34 min) as an oil which was stirred with a solution of 255 ml of 12N hydrochloric acid in 25.5 L of methanol for 30 minutes (pH=1.5). The mixture was then concentrated at 45° C./50 torr to give 12.5 kg (70% of theory) of the title compound (83% pure by GC) which was characterized by $^1H$ NMR and $^{13}C$ NMR. The obtained material was used without further purification in the next step (Example 2).

$^{13}C$ NMR ($CDCl_3$), δ (ppm): 16.43, 16.48, 25.77, 25.92, 32.01, 32.07, 32.45, 32.48, 32.60, 33.66, 33.75, 34.49, 34.56, 34.64, 34.77, 35.97, 36.67, 37.18, 37.86, 49.07, 49.28, 49.48, 60.39, 60.48, 66.64.

Example 2

O-Ethyl (3-amino-(2R)-hydroxypropyl)(cyclohexylmethyl)phosphinate

A solution of the compound of example 1 (12.5 kg, crude) in absolute ethanol (50 L) was charged to a 20 gallon reactor equipped with a pressure gauge. The reactor was cooled to −50° C. and maintained at −50° C. to −35° C. while liquid ammonia (15.5 kg, 912 mol) was added over 90 min. The suspension was slowly warmed to room temperature and left for 4 days with internal pressure at 35–45 psi. The mixture was then filtered to remove ammonium chloride and the filtrate was evaporated at 50° C./50 torr to give the crude title compound (12.2 kg) as a white wax which was characterized by $^1H$ NMR and $^{13}C$ NMR. The obtained material was used without further purification in the next step (Example 3).

$^{13}C$ NMR ($CDCl_3$), δ (ppm): 16.42, 16.50, 25.73, 25.87, 31.93, 31.99, 34.38, 34.53, 34.61, 34.74, 60.18.

Example 3

(3-Amino-(2R)-hydroxypropyl)(cyclohexylmethyl) phosphinic Acid Hydrochloride

A mixture of the compound of example 2 (12.2 kg, crude) and 37% hydrochloric acid (37 L) was heated at reflux (96° C.) for 4 h. A caustic scrubber solution was used to trap hydrogen chloride off-gas. The solution was evaporated to dryness at 60° C./50 torr and co-evaporated sequentially with 30 L each of water, toluene and ethanol to afford the crude title compound (11.7 kg) as an off-white solid which was characterized by $^1H$ NMR and $^{13}C$ NMR. The obtained material was used without further purification in the next step (Example 4).

$^{13}$C NMR (D$_2$O), δ(ppm): 25.45, 25.58, 31.64, 34.04, 34.14, 34.26, 34.39, 35.21, 36.09, 37.29, 45.10, 45.29, 63.00.

Example 4

(3-Amino-(2R)-hydroxypropyl)(cyclohexylmethyl) phosphinic Acid

A mixture of the compound of example 3 (11.7 kg, crude) in absolute methanol (70 L) was treated with charcoal (293 g, 20–40 mesh, from Aldrich) at reflux for 40 min. The mixture was filtered through a cartridge filter (5 micron) and washed with methanol (20 L). The filtrate was cooled to room temperature and treated with triethylamine (5.4 kg, 53.3 mol). A white solid began to form after about 50% of the triethylamine had been added. The suspension was stirred for 20 h, and the solid was collected by filtration and washed with cold methanol (two times, 10 L each). The crude solid was then digested in methanol (two times, 50 L each) for 2 h at 65° C. and allowed to cool to room temperature. The solid was collected by vacuum filtration and washed with methanol (10 L). After drying at 40° C./50 torr for 18 h, 6.5 kg of the crude title compound was obtained. The crude product was dissolved in deionized water (18 L) at 85° C. and the hot solution was filtered through a bed of Celite and rinsed with water (2 L). The filtrate was stirred and acetone (80 L) was added over 45 min. The mixture was kept at 4° C. for 20 h. The precipitated product was filtered off, washed with acetone (two times, 15 L each) and dried (50° C./50 torr) for 48 h to give 5.4 kg of the title compound (37% overall yield from O-ethyl (cyclohexylmethyl)phosphinate) as a fine white crystalline solid which was characterized by Karl Fischer titration, elemental analysis, specific rotation, $^1$H NMR, $^{13}$C NMR, $^{31}$P NMR, and LC/MS.

$^{13}$C NMR (D$_2$O), δ(ppm): 25.59, 25.72, 32.08, 32.13, 34.53, 34.64, 34.76, 35.73, 36.85, 37.94, 39.16, 45.22, 45.36, 63.89.

$^{31}$P NMR (D$_2$O), δ (ppm): 41.63.

Karl Fischer titration: 0.61% water.

$[\alpha]^{25}_D$=+8.16° (c=1.03, H$_2$O).

APCI LC/MS: m/z: 236 (100%, M$^+$+H), 471 (35%, 2M$^+$+1), 706(10%, 3M$^+$+1).

Elemental Analysis: Calculated for C$_{10}$H$_{22}$NO$_3$P× 0.08H$_2$O (236.71): C, 50.74; H, 9.44; N, 5.92; Found: C, 50.81; H, 9.36; N, 5.86.

Example 5

Silylation of O-ethyl (cyclohexylmethyl)phosphinate

To a mixture of O-ethyl (cyclohexylmethyl)phosphinate (79 g, 414 mmol) and hexamethyldisilazane (480 mL, 2.3 mol, 5.5eq.) was added ammonium sulfate (5 g, 9 mol %) and the resulting mixture was heated at 128° C. for 22 h. The reaction mixture was then cooled to room temperature and the obtained intermediate of formula III in which R is cyclohexylmethyl used in the subsequent reaction step.

Example 6

Silylation of O-ethyl (cyclohexylmethyl)phosphinate

A 100 ml 3-necked round bottom flask was charged with 3.0 g (15.8 mmol) of O-ethyl (cyclohexylmethyl)phosphinate, 30 mL (9eq.) of hexamethyldisilazane and 0.5 ml (0.25 eq.) of chlorotrimethylsilane. The mixture was heated at reflux for 16 h under a nitrogen atmosphere. The excess amount of hexamethyldisilazane was removed by vacuum distillation and the obtained intermediate of formula III in which R is cyclohexylmethyl used in the subsequent step.

Example 7

Silylation of O-ethyl Benzylphosphinate

A mixture of O-ethyl benzylphosphinate (0.78 g, 4.23 mmol) and hexamethyldisilazane (5 mL) was heated at 140° C. for 16 h and cooled to room temperature to give the intermediate of formula III in which R is benzyl. The subsequent steps for the preparation of the compound of formula I in which R is benzyl can be performed analogously to the above-described procedures for the preparation of the compound of formula I in which R is cyclohexylmethyl.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for the preparation of a compound of the formula I:

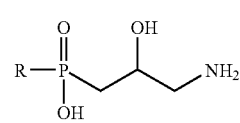

including its enantiomers or diastereomers, which comprises:

(a) reacting a compound of the formula II:

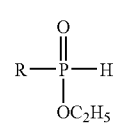

with hexamethyldisilazane to form a compound of formula III:

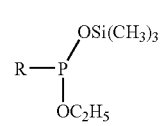

(b) reacting the compound of formula III with epihalohydrin and subsequent hydrolysis of the resulting adduct to form a compound of formula V:

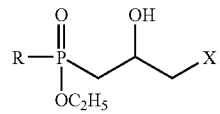

(c) reacting compound of formula V with ammonia and subsequent hydrolysis of the ethyl phosphinate moiety to the compound of formula I, and optionally
(d) converting the compound of formula I into a pharmaceutically acceptable salt,
wherein R is benzyl or cyclohexylmethyl, and X is halogen.

2. The process as set forth in claim 1, wherein the reaction of the compound of formula II with hexamethyldisilazane is carried out in the presence of a catalyst.

3. The process as set forth in claim 2 wherein said catalyst is an ammonium salt.

4. The process as set forth in claim 1 wherein said epihalohydrin is (S)- or (R)-epifluorohydrin, (S)- or (R)-epichlorohydrin, (S)- or (R)-epibromohydrin or (S)- or (R)-epiiodohydrin.

5. The process as set forth in claim 1 wherein said epihalohydrin is (S)- or (R)-epichlorohydrin.

6. The process as set forth in claim 5 wherein said reaction of the compound of formula III with (S)- or (R)-epichlorohydrin is carried out in the presence of a catalyst.

7. The process as set forth in claim 6 wherein a Lewis acid is used as the catalyst.

8. The process as set forth in claim 1 wherein the hydrolysis of the ethyl phosphinate moiety is carried out under acidic conditions.

9. The process as set forth in claim 8 wherein hydrochloric acid is used for the hydrolysis of the ethyl phosphinate moiety.

10. The process as set forth in claim 1 wherein a salt of the compound of formula I obtained in the hydrolysis is converted into the compound of formula I.

11. The process as set forth in claim 10 wherein an acid addition salt of the compound of formula I obtained in the hydrolysis is converted into the compound of formula I by treatment with an amine.

12. The process as set forth in claim 11 wherein said amine is triethylamine.

13. The process as set forth in claim 1 wherein R is cyclohexylmethyl.

14. The process as set forth in claim 1 wherein the compound of formula I having R configuration at the chiral carbon atom is prepared.

15. The process as set forth in claim 1 wherein (3-amino-(2R)-hydroxypropyl)-(cyclohexylmethyl)phosphinic acid of formula Ic is prepared

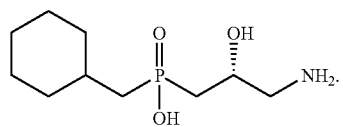

16. The process as set forth in claim 1 wherein (3-amino-(2R)-hydroxypropyl)-(benzyl)phosphinic acid of formula Id is prepared

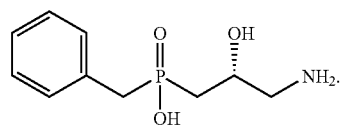

17. The process as set forth in claim 1 wherein the compound of formula I having S configuration at the chiral carbon atom is prepared.

18. The process as set forth in claim 1 in which (3-amino-(2S)-hydroxypropyl)-(cyclohexylmethyl)phosphinic acid of formula Ie is prepared

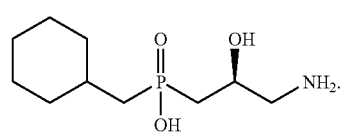

19. The process as set forth in claim 1 in which (3-amino-(2S)-hydroxypropyl)-(benzyl)phosphinic acid of formula If is prepared

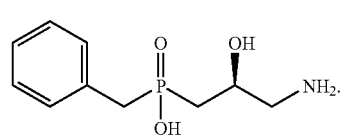

20. A process for the preparation of a compound of the formula Ic:

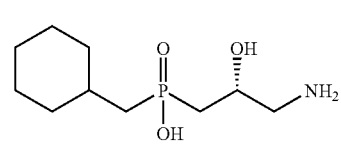

which comprises:
(b) reacting a compound of the formula IIc:

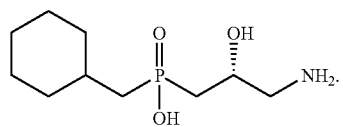

with hexamethyldisilazane to form a compound of formula IIIc:

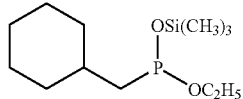

IIIc (b) reacting the compound of formula III with (S)-(+)-epichlorohydrin and subsequent hydrolysis of the resulting adduct to form a compound of formula Vc:

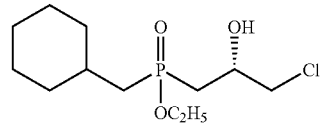

Vc (c) reacting compound of formula Vc with ammonia and subsequent hydrolysis of the ethyl phosphinate moiety to form compound of formula Ic as its hydrochloride; and (d) treating the hydrochloride of compound of formula Ic with an amine to form the compound of formula Ic.

* * * * *